(12) United States Patent
Iyunni (10) Patent No.: US 10,758,382 B2
(45) Date of Patent: Sep. 1, 2020

(54) STENT WITH ONE-WAY SOCK VALVE

(71) Applicant: SaiNath Intellectual Properties, LLC, Pinellas Park, FL (US)

(72) Inventor: Venkata Sesha Sayi Nath Iyunni, Pinellas Park, FL (US)

(73) Assignee: Sainath Intellectual Property, LLC, Pinellas Park, FL (US)

( * ) Notice: Subject to any disclaimer, the term of this patent is extended or adjusted under 35 U.S.C. 154(b) by 0 days.

(21) Appl. No.: 15/573,893

(22) PCT Filed: Jul. 27, 2017

(86) PCT No.: PCT/US2017/044139
§ 371 (c)(1),
(2) Date: Nov. 14, 2017

(87) PCT Pub. No.: WO2018/022862
PCT Pub. Date: Feb. 1, 2018

(65) Prior Publication Data
US 2018/0243114 A1    Aug. 30, 2018

Related U.S. Application Data

(60) Provisional application No. 62/367,496, filed on Jul. 27, 2016.

(51) Int. Cl.
*A61F 2/04*  (2013.01)
*A61F 2/90*  (2013.01)
(Continued)

(52) U.S. Cl.
CPC .................. *A61F 2/90* (2013.01); *A61F 2/04* (2013.01); *A61F 2/82* (2013.01); *A61F 2/24* (2013.01);
(Continued)

(58) Field of Classification Search
CPC .. A61F 2/2412; A61F 2/00; A61F 2/90; A61F 2/2418; A61F 2002/045;
(Continued)

(56) References Cited

U.S. PATENT DOCUMENTS 4,222,126 A * 9/1980 Boretos ................. A61F 2/2412
137/849
4,451,936 A    6/1984 Carpentier et al.
(Continued)

OTHER PUBLICATIONS

Boston Scientific, WallFlex(tm) Esophageal Partially Covered Stent System, 1 page.
(Continued)

*Primary Examiner* — Brian A Dukert
*Assistant Examiner* — Rebecca Lynee Zimmerman
(74) *Attorney, Agent, or Firm* — Eleanor M. Yost; Carlton Fields, PA (57) ABSTRACT

A stent with a one-way sock valve comprises a stent portion and a one-way valve portion. The one-way valve portion comprises a heel portion. The heel portion prevents solids and liquids from entering an opening in the one-way valve portion. Solids and liquids enter the one-way sock valve in a first direction through the stent portion and exit an opening transversely to the longitudinal axis of the stent portion. The sock valve folds, closing the sock valve to any reverse flow in a second direction opposite of the first direction.

4 Claims, 8 Drawing Sheets

(51) Int. Cl.
*A61F 2/82* (2013.01)
*A61M 27/00* (2006.01)
*A61F 2/24* (2006.01)

(52) U.S. Cl.
CPC ... *A61F 2002/041* (2013.01); *A61F 2002/044* (2013.01); *A61F 2210/0066* (2013.01); *A61M 27/002* (2013.01)

(58) Field of Classification Search
CPC .... A61F 5/0076; A61F 2002/077; A61F 2/07; A61F 5/0073; A61F 2/848; F16K 15/14
USPC .............................................. 623/23.68, 23.7
See application file for complete search history.

(56) References Cited

U.S. PATENT DOCUMENTS

| | | | |
|---|---|---|---|
| 5,645,559 | A | 7/1997 | Hachtman et al. |
| 6,302,917 | B1 | 10/2001 | Dua et al. |
| 7,749,011 | B2 * | 7/2010 | Arts ................ H01R 13/748 |
| | | | 439/248 |
| 8,398,704 | B2 | 3/2013 | Straubinger et al. |
| 2002/0151957 | A1 | 10/2002 | Kerr |
| 2002/0198594 | A1 | 12/2002 | Schreck |
| 2004/0102855 | A1 * | 5/2004 | Shank ................ A61F 2/90 |
| | | | 623/23.68 |
| 2006/0111660 | A1 | 5/2006 | Wolf et al. |
| 2006/0142847 | A1 * | 6/2006 | Shaknovich ............ A61F 2/24 |
| | | | 623/1.24 |
| 2007/0016306 | A1 * | 1/2007 | Dua ...................... A61F 2/07 |
| | | | 623/23.68 |
| 2007/0233227 | A1 * | 10/2007 | Greenan ................ A61F 2/07 |
| | | | 623/1.13 |
| 2008/0208314 | A1 * | 8/2008 | Skerven ................ A61F 2/04 |
| | | | 623/1.15 |
| 2009/0254176 | A1 | 10/2009 | Butera |
| 2011/0190905 | A1 | 8/2011 | Behan |
| 2012/0116285 | A1 * | 5/2012 | Duggirala ............ A61F 5/0079 |
| | | | 604/8 |
| 2012/0130468 | A1 | 5/2012 | Khosravi et al. |
| 2013/0023983 | A1 | 1/2013 | Yang et al. |
| 2013/0110253 | A1 | 5/2013 | Gill et al. |
| 2014/0114433 | A1 * | 4/2014 | McHugo ................ A61F 2/04 |
| | | | 623/23.68 |
| 2014/0277428 | A1 * | 9/2014 | Skemp ................ A61F 2/2418 |
| | | | 623/2.42 |

OTHER PUBLICATIONS

Cook, Evolution (registered) Esophageal Stent System—Fully Covered, 2 pages.
http://www.rrnursingschool.biz/chronic-pancreatitis/types-of-esophageal-stents.html, Types of esophageal stents—Chronic Pancreatitis, 1 page.
European Patent Office Search Report for EU Patent Application No. 17835258.9, dated Dec. 6, 2019.

* cited by examiner

STENT WITH ONE-WAY SOCK VALVE

CROSS RELATED APPLICATIONS

This application is a 371 U.S. national phase of International Application PCT/US2017/044139 filed Jul. 27, 2017 which claims priority to U.S. Provisional Appl. No. 62/367,496, which was filed on Jul. 27, 2016, which is hereby incorporated by reference in its entirety.

FIELD OF THE INVENTION

The field relates to stents used in medical procedures, particularly expandable stents for esophageal, pancreatic duct, bile duct and the like.

BACKGROUND

Esophageal stents are known that come in a variety of materials including stainless steel, nickel titanium shape memory alloys, and other proprietary alloys. Such stents may comprise a mesh or zig zag configuration and one or more full or at least partial coverings. Implantation is accomplished using a catheter. The catheter may be size 16 French to 28 French, for example. Post implantation diameter may increase to nearly 3 centimeters, for example. For example, WallFlex™ is Boston Scientific brand of esophageal stent, and Evolution® is a Cook brand of esophageal stent. A multiple layer stent is disclosed in U.S. Pat. No. 5,645,559, for example, which illustrates the way that such stents are positioned using a catheter, for example. U.S. Pat. No. 6,302,917 illustrates an anti-reflux, zig-zag stent with a tubular sleeve extending from a tubular frame. The disclosures and drawings of these references are incorporated herein in their entirety for the purpose of showing how such stents are constructed and inserted. Nothing in the prior art shows a practical one-way stent comprising a collapsible sock that does not invert when back pressure increases.

SUMMARY

A stent comprises a one-way sock. The one-way sock comprises a collapsible sleeve that collapses against reverse pressure, such as pressure caused by the flow of fluids in a reverse flow direction to the normal flow direction, but remains open for fluids and solids that pass through the collapsible sleeve in a preferred direction, opposite of the reverse flow direction. The stent comprises an expandable mesh or lattice and a sock, wherein the sock forms a "heel" or "elbow" portion, such as 22 in FIG. 7, and an opening opposite of the elbow portion.

In one example, a stent with a one-way sock valve comprises a stent portion and a one-way valve portion. The one-way valve portion comprises a heel portion. The heel portion redirects anything passing through the stent in a transverse direction from the longitudinal direction of the stent. This mechanism prevents solids and liquids from entering an opening in the one-way valve portion in a direction opposite of the intended direction of flow, making the sock a one-way valve. For example, solids and liquids may enter the one-way sock valve in a first direction, longitudinally through the stent portion and may exit an opening disposed transversely to the longitudinal axis of the stent portion by way of the heel of the sock portion. When any fluid attempts to reverse direction back through the sock valve, the sock valve folds, closing the sock valve to reverse flow in a direction opposite of the intended direction of flow through the stent.

BRIEF DESCRIPTION OF THE DRAWINGS

The following drawings are illustrative examples and do not further limit any claims that may eventually issue.

When the same reference characters are used, these labels refer to similar parts in the examples illustrated in the drawings.

DETAILED DESCRIPTION

Figure 1:
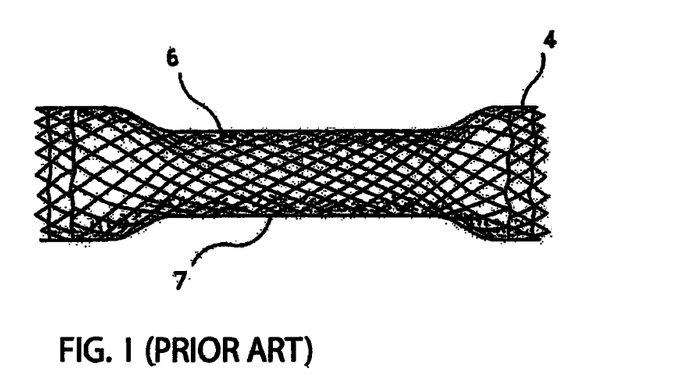
FIG. 1 illustrates a prior art stent.
Figure 2:
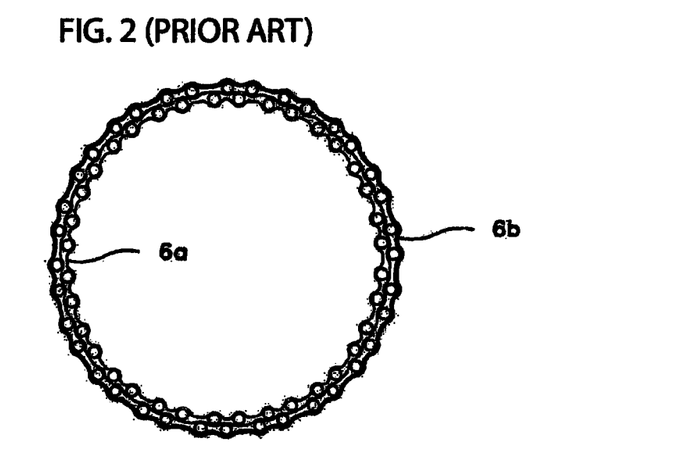
FIG. 2 illustrates another multi-layer prior art stent.
Figure 3:
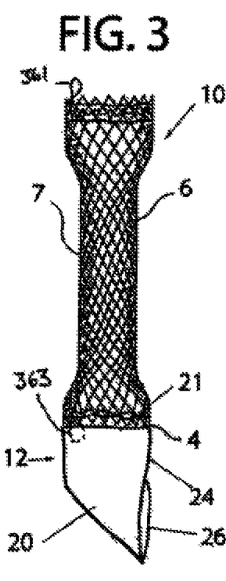
FIG. 3 illustrates a side view of a one-way stent.
Figure 4:
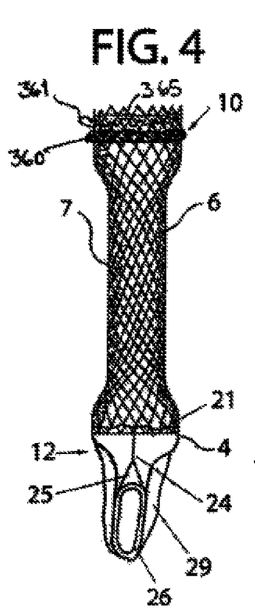
FIG. 4 illustrates a front view of a one-way stent.
Figure 5:
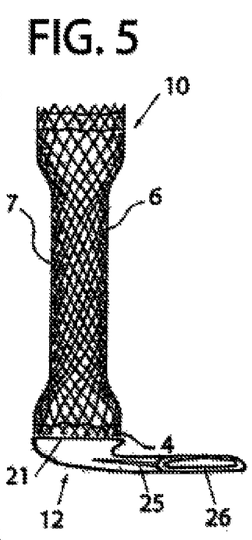
FIG. 5 illustrates another front view of a collapsed one-way stent.
Figure 6:
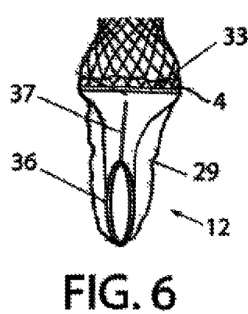
FIG. 6 illustrates a front view of another example of a one-way stent.
Figure 7:
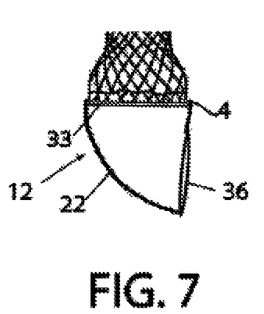
FIG. 7 illustrates a side view of another example of a one-way stent.

A prior art stent 6 shows an expandable mesh or lattice 7 with funnel shaped ends 4, as is known in the art. In one example, In FIGS. 3-7, for example, one-way stents comprise such a mesh or lattice 7, for example. In one example, the one-way stents comprise an expandable retainer ring 360, such as a polyurethane foam. One or more such rings 360 may be provided to help retain the stent in position within a lumen, such as the esophagus. FIG. 2 illustrates a multi-layer stent known in the prior art. The mesh or lattice may be embedded in a layer 6 *a*, 6 *b*, for example. In FIG. 3, a one-way stent comprises a stent 6 with at least one expandable mesh or lattice 7. In addition, a retraction device 361, 363 may be added to the stent to aid in stent removal. For example, the retraction device may be comprised of a loop and a tab, such that an endoscopic tool may grab and pull on the tab 361, 363, which may be attached to a loop 365, which may be a wire or elastic band interwoven through the mesh of the stent, such that when the tab 361, 363 is pulled, the loop closes expandable ends of the stent, aiding in removal. At a first end is a funnel 10, while a second end 21, opposite of the first end, is attached at a first end 4 of a one-way sock 20. The joint 4 may any of a variety of known joints, such as an adhesively coupled joint, an integrally formed joint or a mechanically coupled joint, for example. A front portion 24 may comprise an elastic material or a non-elastic material. The sock 12 may comprise a collapsible portion 25 and an opening 26 that are biased collapsed and closed, respectively, for example, by incorporating an elastic material in the collapsible portion, for example. The sides 29 of the sock may be a fabric or film, for example. FIGS. 5-7 show an alternative structure with a spine 37 that prevents the front portion from folding in one direction but provides for collapsing of the sock to the side, as illustrated in FIG. 5, for example. Alternatively, as illustrated in FIG. 7, no spine is required. An attachment ring 33 may be used to join the sock 12 to a stent 6, for example. FIGS. 6 and 7 show examples where the opening 36 comprises a ring that is at least partially biased open, even when the valve is closed. In one example, this provides for escape of gases from the stomach, even when the valve prevents liquids and solids from entering and passing through the one-way valve in the reverse direction.

Figure 8:
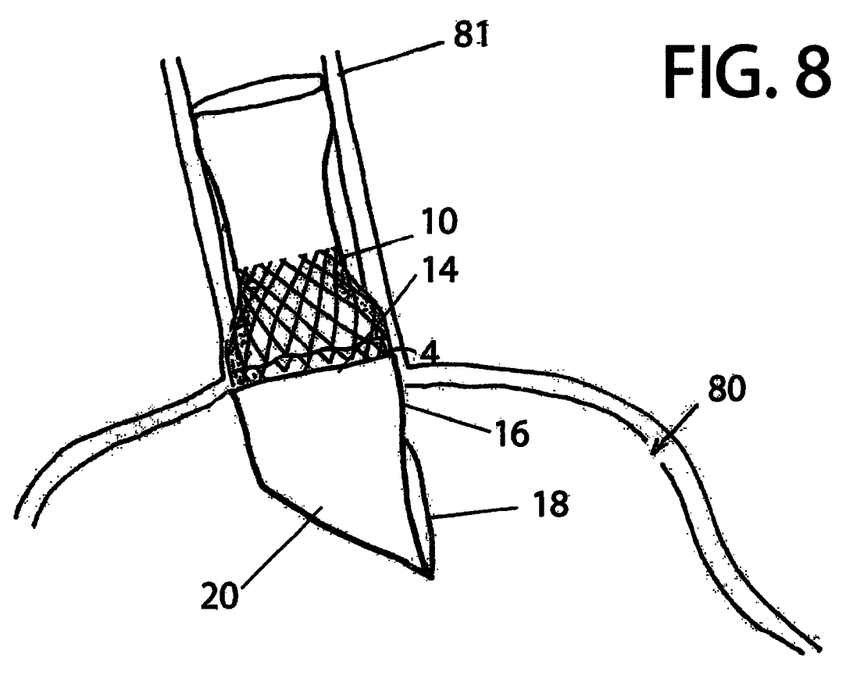
FIG. 8 illustrates a side view of an example of a one-way stent inserted in an esophagus, where the esophagus meets the stomach.
Figure 9:
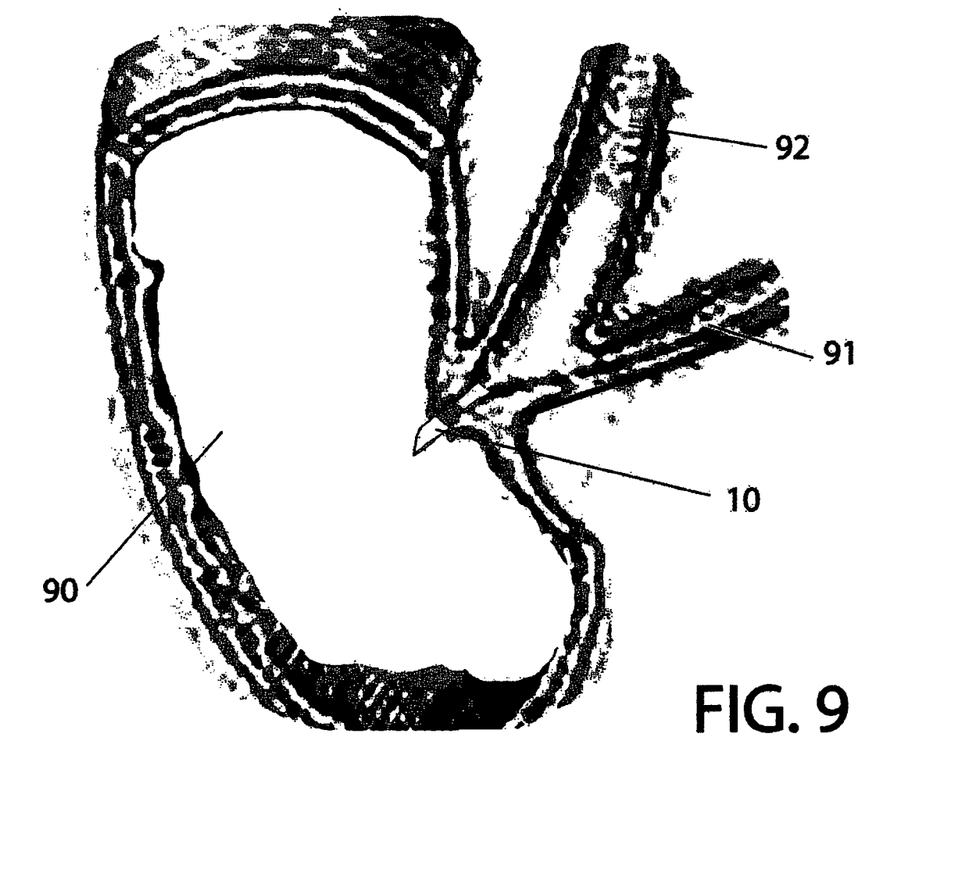
FIG. 9 illustrates a side view of an example of a one-way stent inserted in a bile duct.
Figures 10, 10A:
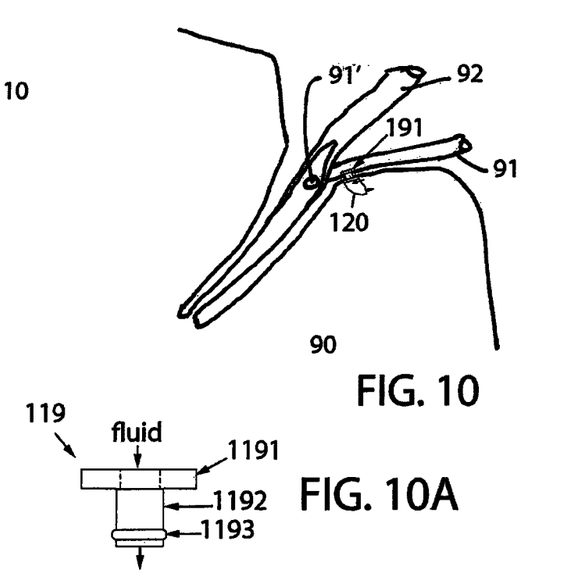
FIGS. 10 and 10A illustrate an example of a one-way stent with snap-on valve utilized as a shunt between a pancreatic duct and the intestinal tract.

FIG. 8 illustrates a stent 10 inserted in an esophagus 81, where the esophagus meets the stomach 80, and the sock 20 extends into the stomach 80. In this example, an attachment region 14 is attached to an end 4 of the stent 10, and the upper portion 16 of the sock 20 is funnel shaped, necking, at least slightly toward the lower portion of the sock 20 where an opening 18 is provided, for example. FIG. 9 shows an alternative example with a stent 10 inserted in a bile duct 92, where the bile duct meets the intestinal tract 90. FIG. 10 illustrates yet another example where the one-way sock valve 120 is used with a bypass shunt stent from the pancreatic duct 91 to the intestinal tract 90. As best shown in FIG. 10A, the shunt stent portion 119 comprises flange 1191, a tubular member 1192 providing fluid flow communication through the shunt stent 119, and a press fit retaining ring 1193, for example. The press fit retaining ring 1193 may be sized to snap fit into the retainer 121 of the one-way sock valve 120, for example. This provides a minimally invasive device for insertion of a shunt stent and valve assembly 191, comprising the shunt stent 119 and a one-way sock valve 120, for example. This may be used when the duct opening 91' of the pancreatic duct 91 becomes blocked, for example. In FIG. 10, the duct opening 91' is shown entering the bile duct 92, for example.

Figure 11:
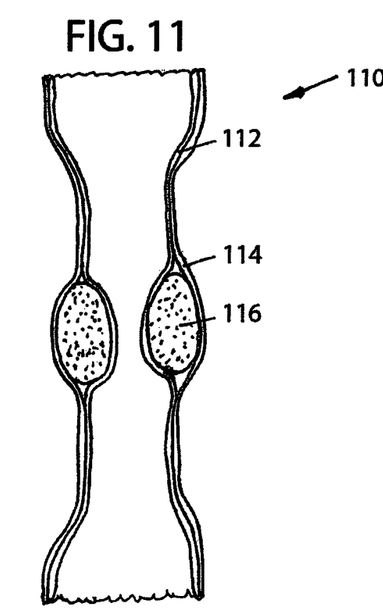
FIG. 11 illustrates an example of a portion of a stent comprising a foam ring.

In the example of FIG. 11, a portion of a stent 110 comprises a compressible foam 116. A compressible foam may be biocompatible or may be entirely enclosed in a biocompatible material 112, 114. The term "foam" means any of the materials referred to in the art as foams including, without limitation, open celled and closed cell foams, foamed plastic materials, cellular plastics, cellular polymers, plastic foams or expanded plastics, such as expanded polyurethane or the like. In foams, the density of the material is reduced by the inclusion of voids within the volume of the foam. Foams are known that may be compressed in volume substantially and recover all or a significant fraction of the original volume when decompressed or released. In some examples, heat, light, moisture or other stimulus is required to expand the foam. One example of a heat activated, compressible foam is an SMP Foam, available from SMP Technologies Inc. (Tokyo, Japan). In one example, the density of a foam may be selected in a range from about 10 kg/m3 to about 60 kg/m3, where about allows for variance expected in the art for such foams. More preferably, the density may be selected for an esophageal in a range from 20 kg/m3 to about 40 kg/m3 in order to slow the progress of food ingestion without fully blocking the passing of food through the stent. The change in volume of a compressed foam to a decompressed foam may be selected, such that the stent may be deployed as is known in the art, in a compressed state, without any substantial changes to the methods of deployment of similar stents. However, when the stent is positioned, the decompressed foam forms a constriction within the stent reducing the rate of flow through the stent. For example, a volume change up to about 100% is possible with compressible foams that are biocompatible. More preferably, a range of volume change from about 500% to about 1000% may be selected. In one example, the foam 116 is shaped into a ring, as illustrated in FIG. 11, for example, and the ring is disposed between an inner layer 112, such as a layer of polyurethane forming the inner wall of the stent, and another layer 114 of the stent forming a layer adjacent to the inner layer. When the stent is compressed, the foam ring is compressed, also. When the stent 110 is deployed, then the foam ring expands to fill a portion of the volume of the stent, constricting the passage through a portion of the stent, as illustrated in FIG. 11, for example.

Figure 12:
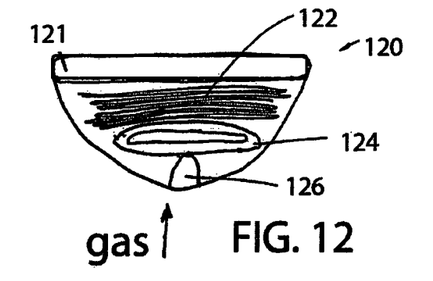
FIG. 12 illustrates yet another front view of a collapsed sock portion of a one-way stent.
Figure 13:
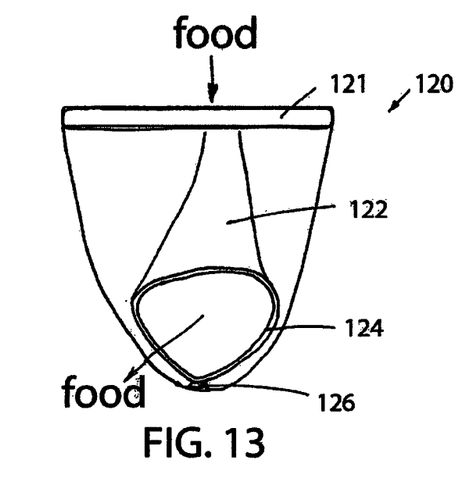
FIG. 13 illustrates a front view of the sock portion of FIG. 12 while food or liquids are passing through the sock portion.
Figure 14:
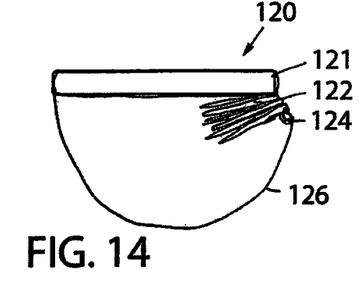
FIG. 14 illustrates a side view of collapsed sock.
Figure 15:
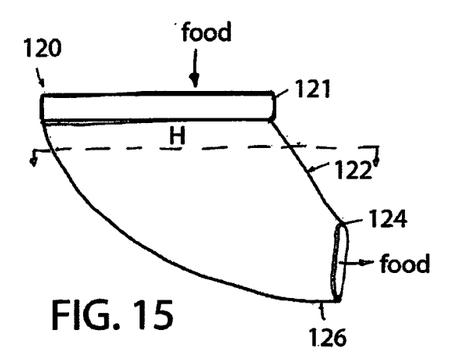
FIG. 15 illustrates a side view of an open sock, while food or drink is passing through the sock.
Figure 16:
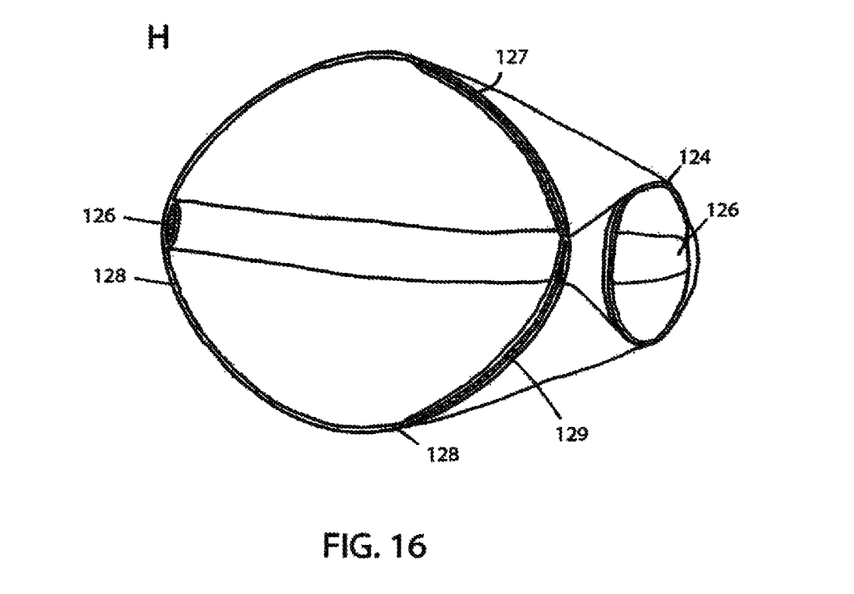
FIG. 16 illustrates a cross sectional view looking down along the dashed line H in FIG. 5.
Figure 17:
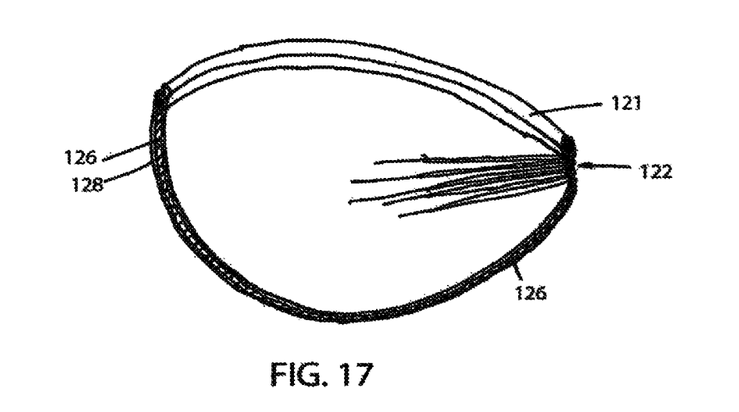
FIG. 17 illustrates a collapsed cross sectional view transverse to the view shown in FIG. 16.
Figures 18, 19:
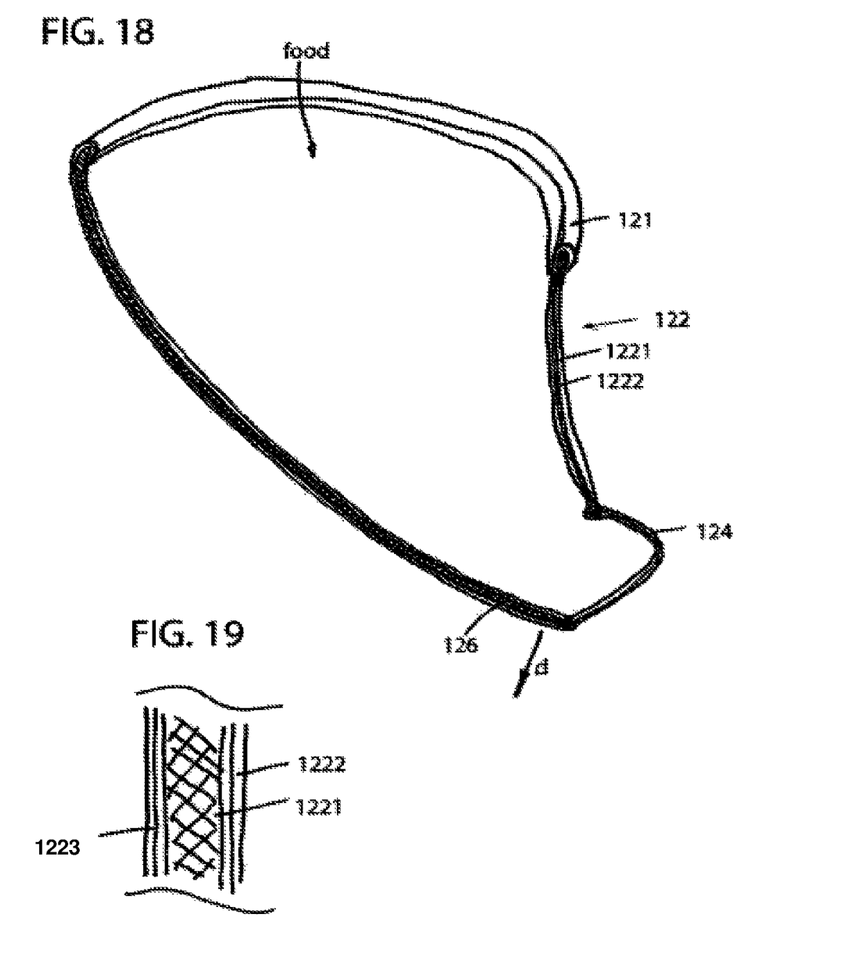
FIG. 18 illustrates an open cross sectional view compared to FIG. 17.
FIG. 19 illustrates an example of a detailed view of a cross section of a collapsible region 120.
Figure 20:
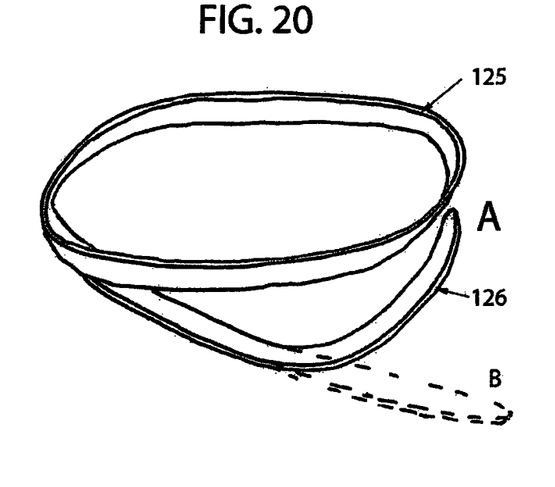
FIG. 20 illustrates a spine integrally formed with a ring retainer, for example.

FIG. 12 illustrates a front, collapsed view of an example of a sock 120 having a retainer 121, a collapsible front portion 122, which may comprise an elastic material, an opening 124, which may be biased closed, as illustrated in FIG. 12, and an elastic spine 126, which may be biased closed, for example. In one example, a gas may pass through the "closed" opening 124, even though liquids and solids are prevented from passing through the opening 124, when biased closed. For example, as illustrated in FIG. 13, the bias closing the opening 124 does not prevent the opening 124 from being open when food or liquids fill the sock 120, and food passes through the sock 120. A side view is illustrated in FIG. 14 that shows how a front portion 122 may be collapsed when the opening 124 is closed. FIG. 15 shows a side view of the opening 124 and sock 120, when the bias of the spine 126 is overcome by the weight of food, for example, or drink. In FIG. 16, a cross sectional view is taken along the dashed line H in FIG. 15, for example. The spine 126 is shown encapsulated in a material of the sock 120. The material is an outer wall 128 and may comprise a elastic layer 129, optionally, to assist in the collapsing of the front portion 122 of the sock that collapses. FIG. 17 illustrates another cross sectional view through a length of the spine 126, when the spine is in the closed position. FIG. 18 illustrates the same cross sectional view as shown in FIG. 17 in the open position. FIG. 19 illustrates a detail of an inner layer 1223, an elastic layer 1221 and an outer layer 1222. The inner and outer layer may be made of a polyurethane or the like, while the elastic layer may be comprised of any elastic material that biases the collapsible portion 122 toward the closed position, such as rubber, elastic mesh or synthetic elastic film. For example, FIG. 20 illustrates a spine 126 integrally formed with a retainer 125 in a first position A (closed) and a second position B (open). For example, the spine may be made of a polyurethane and may be dimensioned to provide for sufficient elasticity to cause the opening in the sock to open when a solid or liquid is present in the sock. In one example, the force applied by the elasticity of the spine and/or the elasticity of the sock is sufficient to close the opening of the sock only when the sock is empty.

The examples may be used in a variety of sizes, and a tubular stent portion may be longer or shorter comparatively to the sock. In one example, the tubular stent portion is shorter than the sock and is used to attach the stent in position using a staple, tacking, staples, suture or sutures. For example, a stent may be disposed in a chamber of a heart, a lung or the like to act as a one-way valve.

This detailed description provides examples including features and elements of the claims for the purpose of enabling a person having ordinary skill in the art to make and use the inventions recited in the claims. However, these examples are not intended to limit the scope of the claims, directly. Instead, the examples provide features and elements of the claims that, having been disclosed in these descriptions, claims and drawings, may be altered and combined in ways that are known in the art.

What is claimed is:

1. A stent comprising a stent portion with a one-way sock valve coupled to the stent portion,
  the stent portion comprising at least one expandable retainer ring present on the surface of the stent portion disposed at the proximal end of the stent portion and a foam ring disposed between a first layer forming the inner wall of the stent portion and a second layer adjacent to the first inner layer, wherein the expandable retainer ring is configured to expand to grip tissue of a lumen of the esophagus in which the stent is deployed and further wherein the foam ring is configured to partially constrict a passage through the stent portion;
  the one-way sock valve comprising a collapsible sleeve,
  wherein the collapsible sleeve collapses against reverse pressure thereby closing the one-way sock valve to flow in a reverse direction to a normal flow direction through the collapsible sleeve and remains open for fluids and solids that pass through the collapsible sleeve in the normal flow direction,
  wherein the sleeve comprises a heel portion,
  wherein the normal flow direction comprises a first direction oriented along a longitudinal axis of the second stent portion within the collapsible sleeve of the one-way sock valve, and a second direction transversely oriented to the first direction,
  wherein fluid and solids passing in the normal flow direction through the one-way sock valve exit from the collapsible sleeve through an opening transversely oriented to the first direction,
  wherein the one-way sock valve further comprising a biasing mechanism,
  wherein the biasing mechanism is arranged such that it biases the one-way sock valve closed, unless the mass of fluid or solids passing through the collapsible sleeve in the normal flow direction overcomes a bias force biasing the collapsible sleeve closed, and
  wherein the biasing mechanism comprises an elastic spine.

2. The stent of claim 1, wherein the stent portion comprises a plurality of expandable retainer rings present on the surface of the stent portion.

3. A stent comprising a stent portion and a one-way sock valve coupled to the stent portion,
  the stent portion comprising:
    an expandable retainer ring present on the outer surface of the stent portion wherein the expandable retainer ring is configured to expand to grip tissue of the lumen of the esophagus; and
    a foam ring disposed between a first layer forming the inner wall of the stent portion and a second layer adjacent to the first inner layer wherein the foam ring is configured to partially constrict a passage through the stent portion,
  the one-way sock valve comprising a collapsible sleeve,
  wherein the collapsible sleeve collapses against reverse pressure thereby closing the one-way sock valve to flow in a reverse direction to a normal flow direction through the collapsible sleeve and remains open for fluids and solids that pass through the collapsible sleeve in the normal flow direction,
  wherein the sleeve comprises a heel portion,
  wherein the normal flow direction comprises a first direction oriented along a longitudinal axis of the stent portion within the collapsible sleeve of the one-way sock valve, and a second direction transversely oriented to the first direction,
  wherein fluid and solids passing in the normal flow direction through the one-way sock valve exit from the collapsible sleeve through an opening transversely oriented to the first direction,
  wherein the one-way sock valve further comprises a biasing mechanism,
  wherein the biasing mechanism is arranged such that it biases the one-way sock valve closed, unless the mass of fluid or solids passing through the collapsible sleeve in the normal flow direction overcomes a bias force biasing the collapsible sleeve closed,
  wherein the biasing mechanism comprises an elastic spine.

4. A stent comprising a stent portion and a one-way sock valve coupled to the stent portion,
  the stent portion comprising:
    a plurality of expandable retainer rings present on the surface of the stent portion wherein the expandable retainer rings are configured to expand to grip tissue of a lumen of the esophagus in which the stent is deployed; and
    a foam ring disposed between a first layer forming the inner wall of the stent portion and a second layer adjacent to the first inner layer wherein the foam ring is configured to partially constrict a passage through the stent portion,
  the one-way sock valve comprising a collapsible sleeve,
  wherein the collapsible sleeve collapses against reverse pressure thereby closing the one-way sock valve to flow in a reverse direction to a normal flow direction through the collapsible sleeve and remains open for fluids and solids that pass through the collapsible sleeve in the normal flow direction,
  wherein the sleeve comprises a heel portion,
  wherein the normal flow direction comprises a first direction oriented along a longitudinal axis of the stent portion within the collapsible sleeve of the one-way sock valve, and a second direction transversely oriented to the first direction,
  wherein fluid and solids passing in the normal flow direction through the one-way sock valve exit from the collapsible sleeve through an opening transversely oriented to the first direction,
  wherein the one-way sock valve further comprising a biasing mechanism,
  wherein the biasing mechanism is arranged such that it biases the one-way sock valve closed, unless the mass of fluid or solids passing through the collapsible sleeve in the normal flow direction overcomes a bias force biasing the collapsible sleeve closed,
wherein the biasing mechanism comprises an elastic spine.

\* \* \* \* \*